United States Patent [19]

Reinehr et al.

[11] Patent Number: 6,015,504
[45] Date of Patent: *Jan. 18, 2000

[54] METHOD FOR INCREASING THE SPF RATING OF TEXTILE FIBERS BY TREATMENT WITH TRIAZINYLDIAMINO STILBENE COMPOUNDS

[75] Inventors: Dieter Reinehr, Kandern, Germany; Claude Eckhardt, Riedisheim, France; Robert Hochberg, Freiburg, Germany; Werner Kaufmann, Rheinfelden, Switzerland; Georges Metzger, Moernach, France

[73] Assignee: Ciba Specialty Chemicals Corporation, Tarrytown, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 09/013,657

[22] Filed: Jan. 26, 1998

Related U.S. Application Data

[62] Division of application No. 08/604,536, Feb. 21, 1996, Pat. No. 5,744,599.

[30] Foreign Application Priority Data

Feb. 22, 1995 [GB] United Kingdom .................. 9503474

[51] Int. Cl.[7] .............................. D06L 3/12; D06P 1/62; D06M 13/262
[52] U.S. Cl. .................................. 252/8.91; 8/110; 8/111; 8/115.51; 8/137; 8/648; 252/8.61; 252/8.84; 252/8.85; 252/8.86; 510/301; 510/303; 510/304; 510/307; 510/308; 510/309; 510/311; 510/312; 510/516; 510/518; 162/158; 162/162
[58] Field of Search .................................. 252/8.61, 8.91, 252/8.84, 8.85, 8.86; 544/193.1, 193.2; 8/115.51, 110, 111, 137, 648; 162/158, 162; 510/301, 303, 304, 307, 308, 309, 311, 312, 516, 518

[56] References Cited

U.S. PATENT DOCUMENTS

| 3,909,441 | 9/1975 | Ohyama et al. ................. 252/300 |
|---|---|---|
| 5,744,599 | 4/1998 | Reinehr et al. ................. 544/193.1 |

FOREIGN PATENT DOCUMENTS

| 0451813 | 10/1991 | European Pat. Off. . |
|---|---|---|
| 0509787 | 10/1992 | European Pat. Off. . |
| 682145 | 11/1995 | European Pat. Off. . |
| 693483 | 1/1996 | European Pat. Off. . |
| 2519654 | 11/1976 | Germany . |
| 3279369 | 12/1991 | Japan . |
| 1286073 | 8/1972 | United Kingdom . |
| 1296080 | 11/1972 | United Kingdom . |
| 1357960 | 6/1974 | United Kingdom . |
| 2518454 | 11/1985 | United Kingdom . |
| 9404515 | 3/1994 | WIPO . |

OTHER PUBLICATIONS

Chem. Abst. 119: 17826 (JP05002241) 1993 No Month.
Chem. Abst. 116: 151801b (JP03279369) 1992 No Month.
Chem. Abst. 115: 242903 (JP03062029) 1991 No Month.
Chem. Abst. 111: 98908 (JP 63282382) 1989 No Month.
Chem. Abst. 75: 7434 (PL 61710) 1971 No Month.
Chem. Abst. 71: 71380 (JP 44008234) 1969 No Month.
Chem. Abst. 68: 31050 (FR 1479540) 1968 No Month.
Chem. Abst. 64: 16055b (NL 6508394) 1966 No Month.
Chem. Abst. 64: 2206a (BE 659350) 1966 No Month.
Chem. Abst. 59: 15421e (FR 1317693) 1963 No Month.
Chem. Abst. 121: 241579 (JP 060003787A2) 1994 No Month.
Chem. Abst. 111: 244134 (JP 010062642A2) 1989 No Month.
Patent Abstracts of Japan, vol. 8, No. 179 32 JP–A–59072442) 1992 No Month.

*Primary Examiner*—Anthony Green
*Attorney, Agent, or Firm*—Kevin T. Mansfield; Jacob M. Levine

[57] ABSTRACT

The present invention relates to new compounds which are useful as ultraviolet absorbing agents (UVAs) and as fluorescent whitening agents (FWAs), and to a method of improving the sun protection factor (SPF) of textile fiber material, especially cotton, polyamide and wool, treated with the new compounds and with certain known compounds.

28 Claims, No Drawings

METHOD FOR INCREASING THE SPF RATING OF TEXTILE FIBERS BY TREATMENT WITH TRIAZINYLDIAMINO STILBENE COMPOUNDS

This is a divisional of prior application Ser. No. 08/604,536 filed Feb. 21, 1996, now U.S. Pat. No. 5,744,599.

The present invention relates to new compounds which are useful as ultraviolet absorbing agents (UVAs) and as fluorescent whitening agents (FWAs), and to a method of improving the sun protection factor (SPF) of textile fiber material, especially cotton, polyamide and wool, treated with the new compounds.

It is known that light radiation of wavelengths 280–400 nm permits tanning of the epidermis. Also known is that rays of wavelengths 280–320 nm (termed UV-B radiation), cause erythemas and skin burning which can inhibit skin tanning.

Radiation of wavelengths 320–400 nm (termed UV-A radiation) is known to induce skin tanning but can also cause skin damage, especially to sensitive skin which is exposed to sunlight for long periods. Examples of such damage include loss of skin elasticity and the appearance of wrinkles, promotion of the onset of erythemal reaction and the inducement of phototoxic or photoallergic reactions.

Any effective protection of the skin from the damaging effects of undue exposure to sunlight clearly needs to include means for absorbing both UV-A and UV-B components of sunlight before they reach the skin surface.

Traditionally, protection of exposed human skin against potential damage by the UV components in sunlight has been effected by directly applying to the skin a preparation containing a UV absorber. In areas of the world, e.g. Australia and America, which enjoy especially sunny climates, there has been a great increase in the awareness of the potential hazards of undue exposure to sunlight, compounded by fears of the consequences of alleged damage to the ozone layer. Some of the more distressing embodiments of skin damage caused by excessive, unprotected exposure to sunlight are development of melanomas or carcinomas on the skin.

One aspect of the desire to increase the level of skin protection against sunlight has been the consideration of additional measures, over and above the direct protection of the skin. For example, consideration has been given to the provision of protection to skin covered by clothing and thus not directly exposed to sunlight.

Most natural and synthetic textile materials are at least partially permeable to UV components of sunlight. Accordingly, the mere wearing of clothing does not necessarily provide skin beneath the clothing with adequate protection against damage by UV radiation. Although clothing containing a deeply coloured dye and/or having a tight weave texture may provide a reasonable level of protection to skin beneath it, such clothing is not practical in hot sunny climates, from the standpoint of the personal comfort of the wearer.

There is a need, therefore, to provide protection against UV radiation for skin which lies underneath clothing, including lightweight summer clothing, which is undyed or dyed only in pale shades. Depending on the nature of the dyestuff, even skin beneath clothing dyed in some dark shades may also require protection from UV radiation.

Such lightweight summer clothing normally has a density of less than 200 g/m² and has a sun protection factor rating between 1.5 and 20, depending on the type of fiber from which the clothing is manufactured.

The SPF rating of a sun protectant (sun cream or clothing) may be defined as the multiple of the time taken for the average person wearing the sun protectant to suffer sun burning under average exposure to sun. For example, if an average person would normally suffer sun burn after 30 minutes under standard exposure conditions, a sun protectant having an SPF rating of 5 would extend the period of protection from 30 minutes to 2 hours and 30 minutes. For people living in especially sunny climates, where mean sun burn times are minimal, e.g. only 15 minutes for an average fair-skinned person at the hottest time of the day, SPF ratings of at least 20 are desired for lightweight clothing.

It is already known, e.g. from WO94/4515, that the application of specified types of UVA to a light-weight textile materials in general can effect an increase in the SPF value of the textile so treated. The increase in SPF value achieved thereby, however, is relatively modest.

The use of FWAs in order to effect an increase in the SPF value of textiles has also been proposed. Most FWAs, however, are only effective in absorbing radiation in the UV-A range.

Certain new compounds have now been found which can be readily produced and which, unexpectedly, absorb radiation in both the UV-A and UV-B ranges, and impart greatly increased SPF ratings to textile fiber materials treated with the new compounds.

Accordingly, the present invention provides, as a first aspect, a compound having the formula:

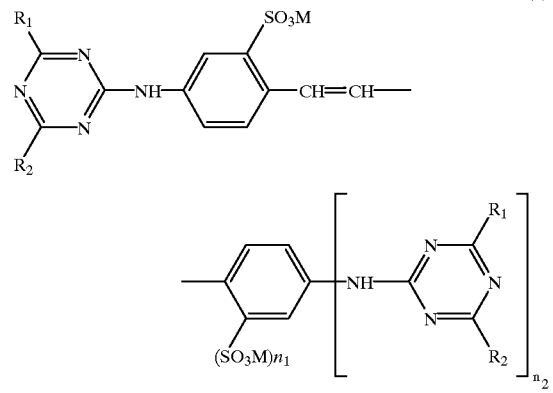

in which M is hydrogen, an alkali metal atom, ammonium or a cation formed from an amine; $R_1$ is a group having one of the formulae:

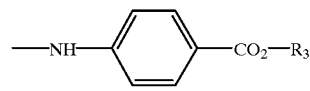

in which $R_3$ is optionally substituted alkyl or optionally substituted aryl;

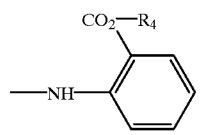

in which $R_4$ is M, optionally substituted alkyl or optionally substituted aryl;

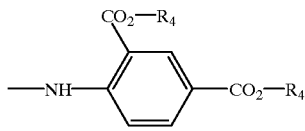

in which $R_4$ has its previous significance;

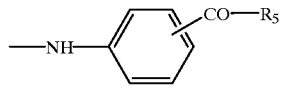

in which $R_5$ is hydrogen, optionally substituted alkyl, optionally substituted aryl or —$NR_7R_8$ in which $R_7$ and $R_8$, independently, are hydrogen, optionally substituted alkyl or optionally substituted aryl, or $R_7$ and $R_8$, together with the nitrogen atom to which they are attached, form a heterocyclic residue, especially a morpholine or piperidine residue;

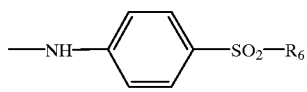

in which $R_6$ is hydrogen, optionally substituted alkyl or optionally substituted aryl, provided that $R_6$ is not carboxymethyl or hydroxymethyl;

$R_2$ is hydrogen, optionally substituted alkyl, optionally substituted aryl,

—$NH_2$, —$N(CH_2CH_2OH)_2$, —$N[CH_2CH(OH)CH_3]_2$, —NH—$R_4$, —$N(R_4)_2$ or —$OR_4$, in which $R_4$ has its previous significance; and $n_1$ and $n_2$, independently, are 0 or 1.

When one or more $R_2$, $R_3$, $R_4$, $R_5$, $R_6$, and $R_7$ and $R_8$ is optionally substituted alkyl, preferred unsubstituted alkyl groups $R_2$, $R_3$, $R_4$, $R_5$, $R_6$, $R_7$ and $R_8$ are $C_1$–$C_{12}$-, especially $C_1$–$C_4$-alkyl groups. The alkyl groups may be branched or unbranched and may be optionally substituted, e.g. by halogen such as fluorine, chlorine or bromine, by $C_1$–$C_4$-alkoxy such as methoxy or ethoxy, by phenol or carboxyl, by $C_1$–$C_4$-alkoxycarbonyl such as acetyl, by a mono- or di-$C_1$–$C_4$alkylated amino group or by —$S)_3M$ in which M has its previous significance.

When one or more of $R_2$, $R_3$, $R_4$, $R_5$, $R_6$, $R_7$ and $R_8$ are optionally substituted aryl, they are preferably a phenyl or naphthyl group which may be substituted by $C_1$–$C_4$-alkyl, e.g. by methyl, ethyl, propyl, isopropyl, butyl, isobutyl, sec.-butyl or tert.-butyl, by $C_1$–$C_4$-alkoxy such as methoxy, ethoxy, propoxy, isopropoxy, butoxy, isobutoxy, sec.-butoxy or tert.-butoxy, by halogen such as fluorine, chlorine or bromine, by $C_2$–$C_5$-alkanoylamino, such as acetylamino, propionylamino or butyrylamino, by nitro, sulpho or by di-$C_1$–$C_4$alkylated amino.

In each of the compounds of formula (1) it is preferred that they are used in neutral form, i.e. that M is other than hydrogen, preferably a cation formed from an alkali metal, in particular sodium, or from an amine.

In the compounds of formula (1), preferably $R_1$ is a group of formula:

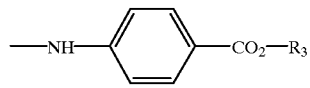

in which $R_3$ has its previous significance and is preferably $C_1$–$C_4$-alkyl, especially methyl or ethyl; or

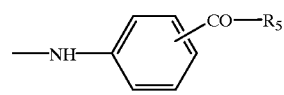

in which $R_5$ has its previous significance and is preferably $C_1$–$C_4$-alkyl, especially methyl or ethyl, or —$NR_7R_8$ in which $R_7$ and $R_8$ have their previous significance and are preferably each hydrogen, $C_1$–$C_4$-alkyl, especially methyl or ethyl, a morpholine or piperidine residue, especially hydrogen; or

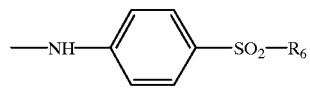

in which $R_6$ has its previous significance and is preferably $C_1$–$C_4$-alkyl substituted by —$SO_3M$, especially methyl or ethyl substituted by —$SO_3M$, in which M has its previous significance and is preferably sodium; and preferably $R_2$ is

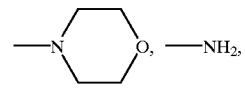

—$N(CH_2CH_2OH)_2$ or —$N[CH_2CH(OH)CH_3]_2$.

The compounds of formula (1) may be produced by reacting, under known reaction conditions, cyanuric chloride, successively, in any desired sequence, with each of an aminostilbene-sulfonic acid, an amino compound capable of introducing a group $R_1$ and a compound capable of introducing a group $R_2$, in which $R_1$ and $R_2$ each have their previous significance.

The starting materials are known compounds which are readily available.

The present invention also provides, as a second aspect, a method for the improvement of the SPF of a textile fiber material, comprising treating the textile fiber material with 0.05 to 3.0% by weight, based on the weight of the textile fiber material, of one or more compounds having the formula:

(1A)

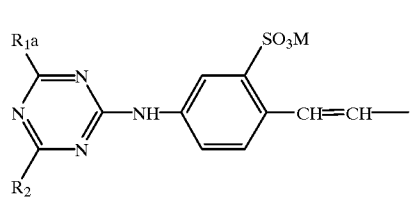

-continued

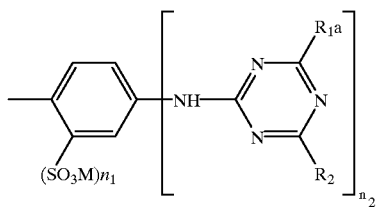

in which $R_2$, $n_1$, $n_2$ and M have their previous significance and $R_1a$ is a group having one of the formulae:

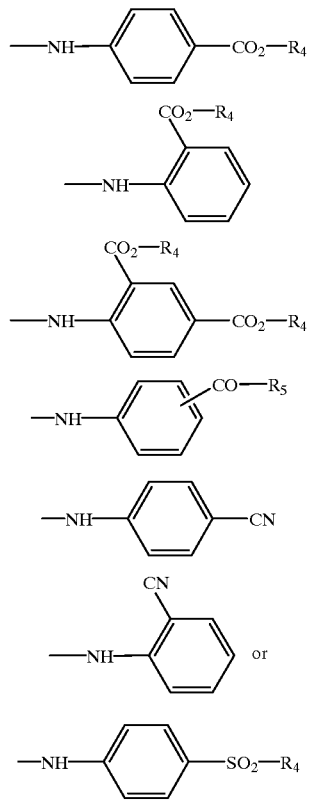

in which $R_4$ and $R_5$ have their previous significance.

The textile fibres treated according to the method of the present invention may be natural or synthetic fibres or mixtures thereof. Examples of natural fibres include vegetable fibres such as cotton, viscose, flax, rayon or linen, preferably cotton and animal fibres such as wool, mohair, cashmere, angora and silk, preferably wool. Synthetic fibres include polyester, polyamide and polyacrylonitrile fibres. Preferred textile fibres are cotton, polyamide and wool fibres.

Preferably, textile fibres treated according to the method of the present invention have a density of less than 200 g/m$^2$ and have not been previously dyed in deep shades.

Some of the compounds of formula (1A) used in the method of the present invention may be only sparingly soluble in water and may need to be applied in dispersed form. For this purpose, they may be milled with an appropriate dispersant, conveniently using quartz balls and an impeller, down to a particle size of 1–2 microns.

As dispersing agents for such sparingly-soluble compounds of formula (1A) there may be mentioned:
acid esters or their salts of alkylene oxide adducts, e.g., acid esters or their salts of a polyadduct of 4 to 40 moles of ethylene oxide with 1 mole of a phenol, or phosphoric acid esters of the adduct of 6 to 30 moles of ethylene oxide with 1 mole of 4-nonylphenol, 1 mole of dinonylphenol or, especially, with 1 mole of compounds which have been produced by the addition of 1 to 3 moles of styrenes on to 1 mole of phenol;

polystyrene sulphonates;

fatty acid taurides;

alkylated diphenyloxide-mono- or -di-sulphonates;

sulphonates of polycarboxylic acid esters;

addition products of 1 to 60, preferably 2 to 30 moles of ethylene oxide and/or propylene oxide on to fatty amines, fatty amides, fatty acids or fatty alcohols, each having 8 to 22 carbon atoms, or on to tri- to hexavalent $C_3$–$C_6$alkanols, the addition products having been converted into an acid ester with an organic dicarboxylic acid or with an inorganic polybasic acid;

lignin sulphonates; and, in particular formaldehyde condensation products, e.g., condensation products of lignin sulphonates and/or phenol and formaldehyde; condensation products of formaldehyde with aromatic sulphonic acids, e.g., condensation products of ditolylethersulphonates and formaldehyde; condensation products of naphthalenesulphonic acid and/or naphthol- or naphthylaminesulphonic acids and formaldehyde; condensation products of phenolsulphonic acids and/or sulphonated dihydroxydiphenylsulphone and phenols or cresols with formaldehyde and/or urea; or condensation products of diphenyloxide-disulphonic acid derivatives with formaldehyde.

Depending on the type of compound of formula (1A) used, it may be beneficial to carry out the treatment in a neutral, alkaline or acidic bath. The method is usually conducted in the temperature range of from 20 to 140° C., for example at or near to the boiling point of the aqueous bath, e.g. at about 90° C.

Solutions of the compound of formula (1A), or its emulsions in organic solvents may also be used in the method of the present invention. For example, the so-called solvent dyeing (pad thermofix application) or exhaust dyeing methods in dyeing machines may be used.

If the method of the present invention is combined with a textile treatment or finishing method, such combined treatment may be advantageously carried out using appropriate stable preparations which contain the compound of formula (1A) in a concentration such that the desired SPF improvement is achieved.

In certain cases, the compound of formula (1A) is made fully effective by an after-treatment. This may comprise a chemical treatment such as treatment with an acid, a thermal treatment or a combined thermal/chemical treatment.

It is often advantageous to use the compound of formula (1A) in admixture with an assistant or extender such as anhydrous sodium sulfate, sodium sulfate decahydrate, sodium chloride, sodium carbonate, an alkali metal phosphate such as sodium or potassium orthophosphate, sodium or potassium pyrophosphate or sodium or potassium tripolyphosphate, or an alkali metal silicate such as sodium silicate.

In addition to the compounds of formula (1A), a minor proportion of one or more adjuvants may also be employed in the method of the present invention. Examples of adjuvants include emulsifiers, perfumes, colouring dyes, opacifiers, further fluorescent whitening agents, bactericides, nonionic surfactants, fabric care ingredients, especially fabric softeners, stain release or stain repellant ingredients or water-proofing agents, anti-gelling agents such as nitrites or nitrates of alkali metals, especially sodium nitrate, and corrosion inhibitors such as sodium silicate.

The amount of each of these optional adjuvants should not exceed 1%, and preferably ranges from 0.01 to 1% by weight on the treated fiber.

The method of the present invention, in addition to providing protection to the skin, also increases the useful life of a textile article treated according to the present invention. In particular, the tear resistance and/or lightfastness of the treated textile fiber material may be improved.

The present invention also provides a textile fabric produced from a fiber treated according to the method of the present invention as well as an article of clothing produced from the said fabric.

Such textile fabrics and articles of clothing produced from the said fabrics typically have an SPF rating of 20 and above whereas untreated cotton, for example, generally has an SPF rating of from 2 to 4.

The treatment method according to the present invention may also be conducted by washing the textile fiber material with a detergent containing at least one compound of formula (1A), thereby imparting an excellent sun protection factor to the fiber material so washed.

The detergent treatment according to the present invention is preferably effected by washing the textile fiber material at least once with the detergent composition at a temperature ranging from 10 to 100° C., especially from 15 to 60° C.

The detergent composition used preferably comprises:

i) 5–90%, preferably 5–70% of an anionic surfactant and/or a nonionic surfactant;
ii) 5–70%, preferably 5–40% of a builder;
iii) 0–30%, preferably 1–12% of a peroxide;
iv) 0–10%, preferably 1–6% of a peroxide activator and/or 0–1%, preferably 0.1–3% of a bleaching catalyst;
v) 0.005–2%, preferably 0.01–1% of at least one compound of formula (1A) ; and
vi) 0.005–10%, preferably 0.1–5% of of one or more auxiliaries, each by weight, based on the total weight of the detergent.

The said detergent compositions are also new and, as such form a further aspect of the present invention.

The detergent may be formulated as a solid, as an aqueous liquid comprising 5–50, preferably 10–35% water or as a non-aqueous liquid detergent, containing not more than 5, preferably 0–1 wt. % of water, and based on a suspension of a builder in a non-ionic surfactant, as described, e.g., in GB-A-2158454.

The anionic surfactant component may be, e.g., a sulphate, sulphonate or carboxylate surfactant, or a mixture of these.

Preferred sulphates are alkyl sulphates having 12–22 carbon atoms in the alkyl radical, optionally in combination with alkyl ethoxy sulphates having 10–20 carbon atoms in the alkyl radical.

Preferred sulphonates include alkyl benzene sulphonates having 9–15 carbon atoms in the alkyl radical.

In each case, the cation is preferably an alkali metal, especially sodium.

Preferred carboxylates are alkali metal sarcosinates of formula $R\text{—}CO(R^1)CH_2COOM^1$ in which R is alkyl or alkenyl having 9–17 carbon atoms in the alkyl or alkenyl radical, $R^1$ is $C_1$–$C_4$ alkyl and $M^1$ is alkali metal.

The nonionic surfactant component may be, e.g., a condensate of ethylene oxide with a $C_9$–$C_{15}$ primary alcohol having 3–8 moles of ethylene oxide per mole.

The builder component may be an alkali metal phosphate, especially a tripolyphosphate; a carbonate or bicarbonate, especially the sodium salts thereof; a silicate or disilicate; an aluminosilicate; a polycarboxylate; a polycarboxylic acid; an organic phosphonate; or an aminoalkylene poly (alkylene phosphonate); or a mixture of these.

Preferred silicates are crystalline layered sodium silicates of the formula $NaHSi_mO_{2m+1} \cdot pH_2O$ or $Na_2Si_mO_{2m+1} \cdot pH_2O$ in which m is a number from 1.9 to 4 and p is 0 to 20.

Preferred aluminosilicates are the commercially-available synthetic materials designated as Zeolites A, B, X, and HS, or mixtures of these. Zeolite A is preferred.

Preferred polycarboxylates include hydroxypolycarboxylates, in particular citrates, polyacrylates and their copolymers with maleic anhydride.

Preferred polycarboxylic acids include nitrilotriacetic acid and ethylene diamine tetra-acetic acid.

Preferred organic phosphonates or aminoalkylene poly (alkylene phosphonates) are alkali metal ethane 1-hydroxy diphosphonates, nitrilo trimethylene phosphonates, ethylene diamine tetra methylene phosphonates and diethylene triamine penta methylene phosphonates.

Any peroxide component may be any organic or inorganic peroxide compound, described in the literature or available on the market, which bleaches textiles at conventional washing temperatures, e.g. temperatures in the range of from 5° C. to 90° C. In particular, the organic peroxides are, for example, monoperoxides or polyperoxides having alkyl chains of at least 3, preferably 6 to 20, carbon atoms; in particular diperoxydicarboxylates having 6 to 12 C atoms, such as diperoxyperazelates, diperoxypersebacates, diperoxyphthalates and/or diperoxydodecanedioates, especially their corresponding free acids, are of interest. It is preferred, however, to employ very active inorganic peroxides, such as persulphate, perborate and/or percarbonate. It is, of course, also possible to employ mixtures of organic and/or inorganic peroxides. The peroxides, especially the inorganic peroxides, are preferably activated by the inclusion of an activator such as tetraacetyl ethylenediamine or nonoyloxybenzene sulfonate. Bleaching catalysts which may be added include, e.g., enzymatic peroxide precursors and/or metal complexes. Preferred metal complexes are manganese or iron complexes such as manganese or iron phthalocyanines or the complexes described in EP-A-0509787.

The detergents used will usually contain one or more auxiliaries such as soil suspending agents, for example sodium carboxymethylcellulose; salts for adjusting the pH, for example alkali or alkaline earth metal silicates; foam regulators, for example soap; salts for adjusting the spray drying and granulating properties, for example sodium sulphate; perfumes; and also, if appropriate, antistatic and softening agents; such as smectite clays; enzymes, such as amylases and proteases; photobleaching agents; pigments; and/or shading agents. These constituents should, of course, be stable to any bleaching system employed.

Compounds of the formula (1A) have also been found to be useful for the fluorescent whitening of textile materials, in which connection polyamides, wool and cotton should be singled out particularly, and of paper.

Certain of the compounds of formula (1A), in particular those containing a group $R_1$ and/or $R_2$ having the formula

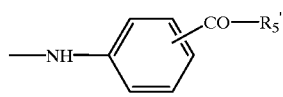

in which $R_5$ is hydrogen, optionally substituted alkyl or optionally substituted aryl, while improving the sun protection factor of textiles treated with them, are non-fluorescent. Such non-fluorescent compounds of formula (1A) are especially suitable for use in textile detergent or softener compositions which dispense with the use of a fluorescent whitening agent in order to maximise the colour care performance of the compositions. Such textile detergent or softener compositions comprising a non-fluorescent compound of formula (1A) form a further aspect of the present invention.

The following Examples further illustrate the present invention.

EXAMPLE 1(A)

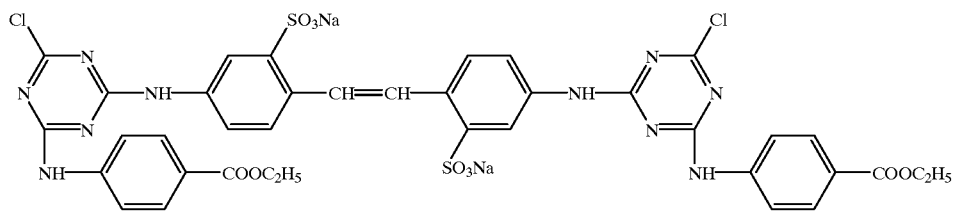

(101)

18.4 g of cyanuric chloride are dissolved in 120 mls. of acetone and 100 g. of ice, cooled to −5° C. and treated, dropwise, with a solution of 25.4 g. of 4,4'-diaminostilbene-2,2'-disulfonic acid in 200 mls. of water and 50 g. of ice. After the addition of 50 mls. of a 1M solution of soda, 16.4 g. of 4-aminobenzoic acid ethyl ester are added. Finally 50 mls. of a 1M solution of soda are added. The resulting suspension is then stirred for 24 hours, during which time the temperature rises to 20° C. The precipitate which forms is filtered off, washed with water and dried giving 45 g. of a yellowish product.

Elemental analysis of the compound having the formula (101) and having the empirical formula $C_{38}H_{30}Cl_2N_{10}Na_2O_{10}S_2.6.5H_2O.1$ NaCl gives: Req. % C 40.0; H 3.77; N 12.28; Cl 9.34; $H_2O$ 10.26. Found % C 40.0; H 3.8; N 12.3; Cl 9.2; $H_2O$ 10.0.

EXAMPLE 1(B)

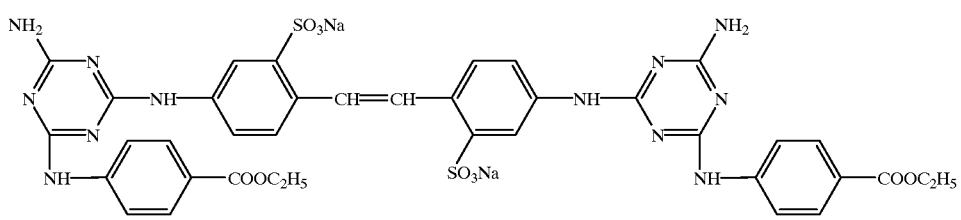

(102)

9.3 g. of the product obtained in Example 1(A) are dissolved in 100 mls. of dioxan, treated with 10 mls. of a 25% aqueous ammonia solution and stirred for 10 hours at 80–90° C. The yellow solution so obtained is then added to 1 liter of isopropanol and filtered. After drying, there are obtained 5.6 g. of a yellow powder having $\lambda_{max}$ values of 304 and 353.

Elemental analysis of the compound having the formula (102) and having the empirical formula $C_{38}H_{34}N_{12}Na_2O_{10}.6.91H_2O$ gives: Req. % C 43.33; H 4.58; N 15.96; S 6.09; $H_2O$ 11.82. Found % C 42.7; H 4.5; N 15.9; S 6.3; $H_2O$ 11.82.

EXAMPLES 2 AND 3

In a manner similar to that described in Example 1, the following further compounds of formula (1) are prepared:

| | (103) |
|---|---|

Structure (103): Triazine-NH-phenyl(SO₃M)-CH=CH-phenyl(SO₃M)-NH-triazine, with R₁, R₂ substituents on each triazine.

| Example | R₁ | R₂ | λ_max |
|---|---|---|---|
| 2 | —NH—C₆H₄—CO₂C₂H₅ | —N[CH₂CH(OH)CH₃]₂ | 305/350 |
| 3 | —NH—C₆H₄—SO₂(CH₂)₂OSO₃Na | —N(morpholino)—O | 293/356 |

EXAMPLE 4

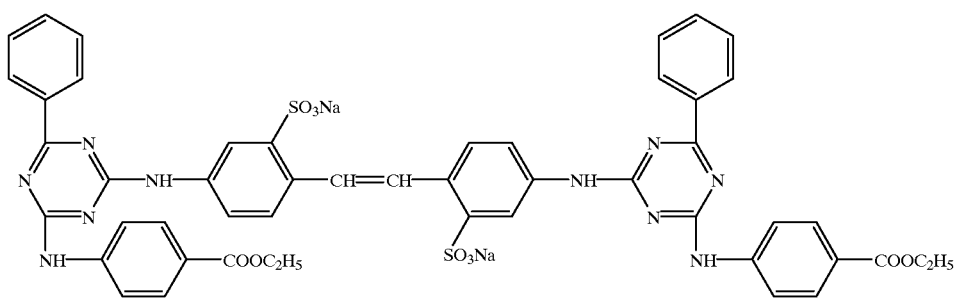

(104)

A) 11.3 g. of 2,4-dichloro-6-phenyl-1,3,5-triazine in 250 mls. of acetophenone are treated with 20 mls. of deionised water. The mixture is adjusted to pH 6.5 with 10 mls. of 2N aqueous caustic soda and 8.3 g. of 4-aminobenzoic acid ethyl ester in 50 mls. of acetophenone are added, dropwise, at 15–20° C. During this addition, the pH is held at between 6.3 and 7 by the addition of 2N aqueous caustic soda. The mixture is stirred for 4 hours and treated with a further 0.5 g. of 4-aminobenzoic acid ethyl ester in 10 mls. of acetophenone and stirred for 2 hours, the pH being held constant by the addition of 2N aqueous caustic soda. The resulting white precipitate is filtered off, dispersed in 250 mls. of acetonitrile, again filtered off and re-washed with 50 mls. of acetonitrile. Finally, the precipitate is dispersed in 250 mls. of cold water, stirred for 15 minutes, filtered and dried in vacuum at 50° C. In this way, there are obtained 13.5 g. of a white product.

B) 7.1 g. of the white product so obtained are dissolved in 100 mls. of dimethylformamide, treated with 3.7 g. of 4,4'-diaminostilbene-2,2'-disulfonic acid and 2 mls. of water and, after the addition of 3 g. of soda, stirred for 24 hours at 105–110° C. The reaction mixture is then completely evaporated in vacuum, taken up in 150 mls. of a 5% w/v aqueous solution of sodium chloride and filtered. The yellow residue is heated to 80° C. in 200 mls. of water, filtered off and boiled three times in a total of 1800 mls. of a methylethylketone-water mixture (1:4) and filtered hot. After drying in vacuum at 60° C., 7 g. of a yellow powder are obtained having $\lambda_{max}$ values of 299.2 and 363.2 and ¹H-NMR (DMSO): δ(in ppm) 10.21 and 10.08 (2H, —HN—), 8.55–7.6 (13H, aromatic and —CH=), 4.31 (2H, —OCH₂—), 1.34 (3H, —CH₃).

EXAMPLE 5

In a manner similar to that described in Example 4, the following further compound of formula (1) is prepared:

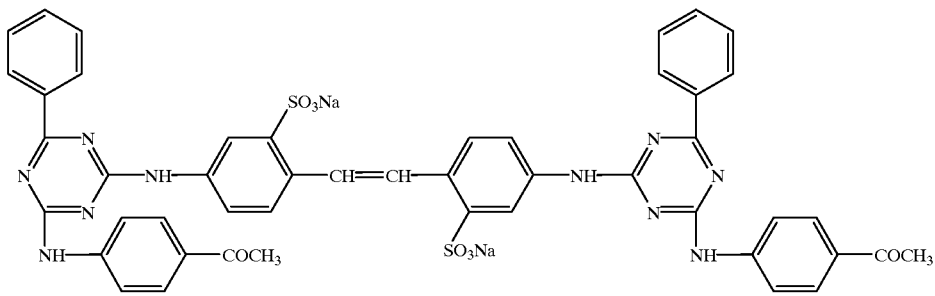
(105)

having $\lambda_{max}$ values of 360.8 and 319.2.

EXAMPLE 6

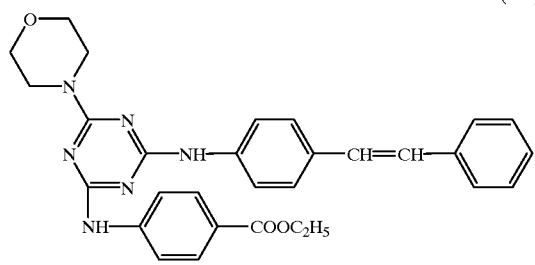
(106)

4.8 g. of cyanuric chloride and 50 g. of ice are added to 100 mls. of acetone. The mixture so obtained is cooled to −15 to −10° C. and treated, dropwise over 30 minutes, with a solution of 7.5 g. 4-aminostilbene-2-sulphonic acid and 13.5 mls. of 1M soda in 40 mls. of deionised water. A further 13 mls. of the soda solution are then added, dropwise over 30 minutes, and the mixture is stirred for a further 30 minutes at −5° C. To this mixture there are then added 4.3 g. of 4-aminobenzoic acid ethyl ester and 13 mls. of the soda solution are added, dropwise, over 30 minutes, whereupon the temperature rises to 25° C. After stirring for 16 hours, 5.66 g. of morpholine are added and the mixture is stirred for 5 hours at 25° C. After removing the acetone in vacuum, a brown solid is filtered off, stirred in 200 mls. of acetone at 40–45° C., filtered and washed with a little ethanol. After drying in vacuum, 7.7 g. of a white solid are obtained having $\lambda_{max}$ values of 307 nm/ϵ 43353 and 331 nm/ϵ 43645.

EXAMPLE 7

The procedure described in Example 1(A) is repeated except that 13.5 g of 4-aminoacetophenone are used instead of 16.4 g of 4-aminobenzoic acid ethyl ester. The intermediate product is not isolated, rather it treated directly with 52.6 g of diethanolamine, warmed to 60° C. and stirred for 15 hours at this temperature. After filtering the reaction mixture and drying, there are obtained 47.8 g of a yellow powder having $\lambda_{max}$ values of 307 nm and 331 nm.

Elemental analysis of the compound having the formula (107) and the empirical formula $C_{44}H_{46}N_{12}Na_2O_{12}S_2.6.35.H_2O$ gives: Req. % C 45.58; H 5.10; N 14.50; S 5.53; $H_2O$ 9.87. Found % C 47.2; H 5.0; N 14.9; S 5.5; $H_2O$ 9.87.

EXAMPLE 8

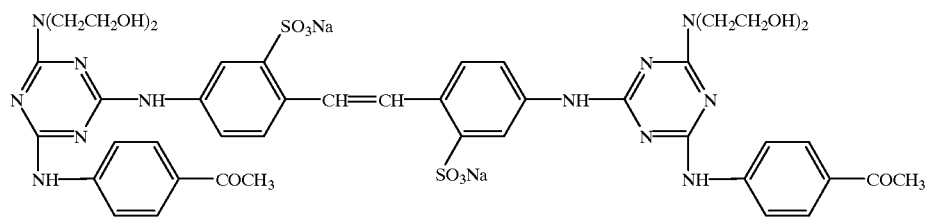
(107)

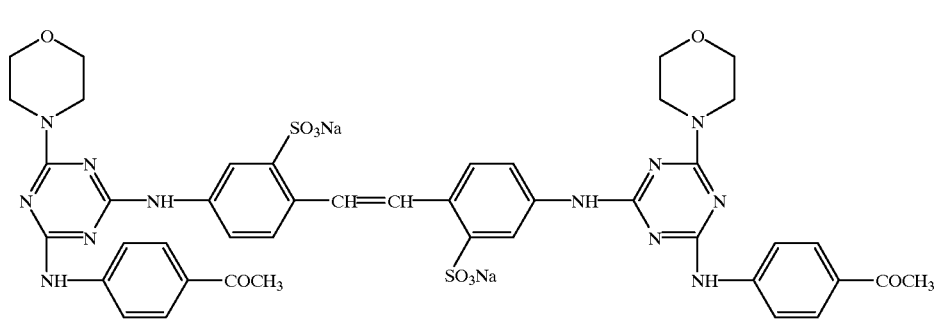
(108)

The procedure described in Example 7 is repeated except that, instead of 52.6 g of diethanolamine, there are used 43.6 g of morpholine. After working up the reaction mixture as described in Example 7, there are obtained 42.0 g of a yellow powder having $\lambda_{max}$ values of 325 nm and 350 nm.

Elemental analysis of the compound having the formula (108) and the empirical formula $C_{44}H_{42}N_{12}Na_2O_{10}S_2.5.47.H_2O$ gives: Req. % C 46.3; H 4.6; N 14.73; S 5.61; $H_2O$ 8.64. Found % C 46.3; H 5.1; N 14.6; S 5.5; $H_2O$ 8.63.

EXAMPLE 9

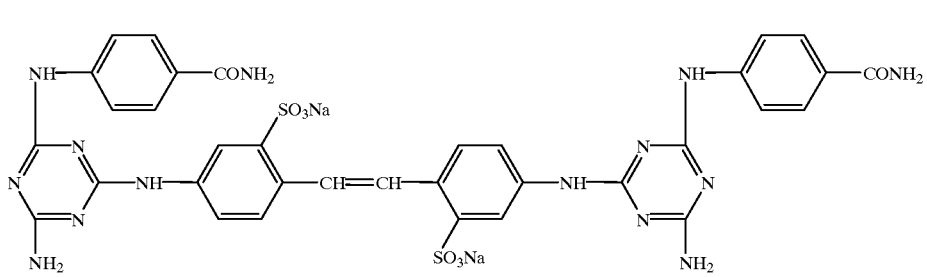
(109)

The procedure described in Example 1(A) is repeated except that the equivalent amount of 4-aminobenzamide is used instead of 16.4 g of 4-aminobenzoic acid ethyl ester. The product so obtained is then reacted with ammonia as described in Example 1(B). After working up the product as described in Example 1(B), compound (109) is obtained in a yield of 91% of theory and has $\lambda_{max}$ values of 298 nm and 358 nm.

Elemental analysis of the compound having the formula (109) and the empirical formula $C_{34}H_{22}N_{14}O_8S_2.6.3.H_2O$ gives: Req. % C 43.45; H 4.56; N 20.86; S 6.82; $H_2O$ 12.04. Found % C 43.4; H 4.44; N 20.78; S 6.93; $H_2O$ 12.03.

EXAMPLE 10

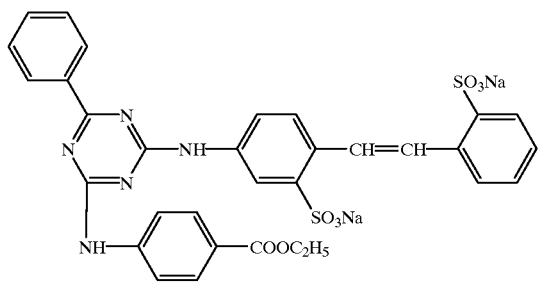
(110)

6 g of the white chlorotriazine intermediate product of Example 4A) are dissolved in 100 mls of dimethylformamide and treated with 8 g of 4-amino-2,2' disulfonic acid. To this mixture are added 2 mls of water and 2 g of soda and the whole is heated for 6 hours at 105–110° C. The solvent is then distilled off in vacuum, the residue is treated with 100 mls each of 5% and with saturated salt solution and filtered. The residue is boiled in 250 mls methylethylketone/water (4:1), filtered hot and dried at 60° C. in vacuum. Finally, the dried product is boiled with 70 mls methylethylketone, filtered hot and dried at 60° C. in vacuum, to give 1 g of the compound of formula (110) as a white powder, having the following analysis:

$_1$H-NMR (MeOD): δ(in ppm)=8.63 (1H, aromatic), 8.46 (2H, aromatic), 8.16 (2H, —CH=CH—), 8.05–7.9 (7H, aromatic), 7.85 (1H, aromatic), 7.64–7.48 (4H, aromatic), 7.35 (1H, aromatic), 4.34 (2H, —OCH$_2$—), 1.39 (3H, —CH$_3$).

UV (MeOH): $\lambda_{max}$ 322 nm/ε 28453.

By concentrating and boiling the filtrate from the final filtration in methylethylketone, a further 3 g of the compound of formula (110) are obtained.

EXAMPLE 11

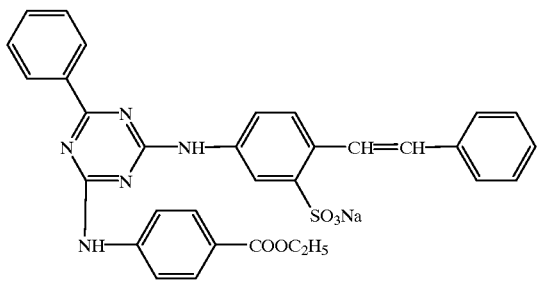

(111)

Using an analogous procedure to that described in Example 10, compound (111) is obtained in a yield of 48% of theory and has the following analysis: $^1$H-NMR (MeOD): δ(in ppm)=8.75 (1H, aromatic), 8.52 (2H, aromatic), 8.26 (1H, —CH=), 8.00 (4H, aromatic), 7.83 (2H, aromatic), 7.64 (2H, aromatic), 7.60–7.48 (3H, aromatic), 7.35 (2H, aromatic), 7.23 (1H, aromatic), 7.11 (1H, —CH=), 4.36 (2H, —OCH$_2$—), 1.40 (3H, —CH$_3$).

UV (MeOH): $\lambda_{max}$ 330 nm/ε 32629.

EXAMPLES 12 TO 14

10 g. of cotton fabric swatches are treated in a 200 ml. aqueous solution with either 0 or 0.2% by weight of the test compound (based on the weight of the cotton) and 1 g. of crystalline sodium sulphate, warmed to 20–60° C. over 10 minutes, held at 60° C. for 20 minutes and cooled from 60° C. to 40° C. over 10 minutes. The swatches are then rinsed in cold tap water, dried and ironed.

The Sun Protection Factor (SPF) is determined by measurement of the UV light transmitted through the swatch, using a double grating spectrophotometer fitted with an Ulbricht bowl. Calculation of SPF is conducted as described by B. L. Diffey and J. Robson in J. Soc. Cosm. Chem. 40 (1989), pp. 130–131.

The average of 5 measurements at different points on each swatch) are shown in the following Table 1:

TABLE 1

| Example | Test Compound | SPF |
|---------|---------------|-----|
| — | none (control) | 5.5 |
| 12 | compound (102) | 36.5 |
| 13 | compound (108) | 27 |
| 14 | compound of Example 3 | 29 |

Compared with the control experiment, the SPF values obtained according to the invention are 5–7 higher.

EXAMPLE 15

A standard (ECE) washing powder is made up from the following components in the indicated proportions (weight %):

| | |
|---|---|
| 8.0% | Sodium (C$_{11.5}$)alkylbenzene sulfonate |
| 2.9% | Tallow alcohol-tetradecane-ethylene glycol ether (14 mols EO) |
| 3.5% | Sodium soap |
| 43.8% | Sodium tripolyphosphate |
| 7.5% | Sodium silicate |
| 1.9% | Magnesium silicate |
| 1.2% | Carboxymethyl cellulose |
| 0.2% | EDTA |
| 21.2% | Sodium sulfate |
| 0 or 0.2% | compound (102) and Water to 100%. |

A wash liquor is prepared by dissolving 0.8 g. of the above washing powder in 200 mls. of tap water. 10 g. of bleached cotton fabric is added to the bath and washed at 30° C., 60° C. or 90° C. over 15 minutes and then rinsed, spin-dried and ironed at 160° C. This washing procedure is repeated up to five times.

After the first, third and fifth washes, the whiteness of the washed samples is measured with a DCI/SF 500 spectrophotometer according to the Ganz method. The Ganz method is described in detail in the Ciba-Geigy Review, 1973/1, and also in the article "Whiteness Measurement", ISCC Conference on Fluorescence and the Colorimetry of Fluorescent Materials, Williamsburg, February 1972, published in the Journal of Color and Appearance, 1, No.5 (1972).

The results obtained are set out in the following Table 2:

TABLE 2

| | | Ganz Whiteness Washing conditions/Temperature and number of washes | | | | | | | | |
|---|---|---|---|---|---|---|---|---|---|---|
| | Amount of test | 30 C. wash | | | 60 C. wash | | | 90 C. wash | | |
| Example | compound | 1x | 3x | 5x | 1x | 3x | 5x | 1x | 3x | 5x |
| — | none | 69 | 69 | 70 | 69 | 70 | 70 | 70 | 71 | 72 |
| 15 | 0.2% | 166 | 191 | 200 | 173 | 199 | 207 | 177 | 203 | 208 |

The results in Table 2 demonstrate that washing with a detergent containing a compound of formula (102) increases the Ganz Whiteness (GW) with successive washings.

EXAMPLES 16 TO 20

The test procedure described in Example 15 is repeated but including a 40 C. wash instead of a 90 C. wash and also determining the respective SPF values of the washed cotton samples. The results obtained are set out in the following Table 3.

TABLE 3

| Example | Test cpd. | Amount of test cpd. | Number of washes | Wash temp. C. | GW | SPF |
|---|---|---|---|---|---|---|
| — | none | — | 3 | 30 | 69 | 2.7 |
| | | | 5 | 30 | 69 | 2.9 |
| | | | 10 | 30 | 70 | 3.0 |
| | | | 3 | 40 | 69 | 2.7 |
| | | | 10 | 40 | 70 | 3.0 |
| | | | 5 | 60 | 70 | 3.1 |
| 16 | cpd.(102) | 0.2% | 3 | 30 | 190 | 10 |
| | | | 5 | 30 | 200 | 17 |
| | | | 10 | 30 | 199 | 22 |
| | | | 3 | 40 | 188 | 12 |
| | | | 10 | 40 | 207 | 28 |
| | | | 5 | 60 | 207 | 20 |
| 17 | cpd.(109) | 0.2% | 3 | 40 | 207 | 13 |
| | | | 10 | 40 | 230 | 31 |
| 18 | cpd.(110) | 0.2% | 3 | 40 | 74 | 11 |
| | | | 10 | 40 | 74 | 13 |
| | | 0.25% | 3 | 30 | 72 | 11 |
| | | | 5 | 30 | 72 | 14 |
| | | | 3 | 60 | 74 | 10 |
| | | | 5 | 60 | 73 | 12 |
| 19 | cpd.(111) | 0.25% | 3 | 30 | 73 | 6 |
| | | | 5 | 30 | 76 | 7 |
| | | | 3 | 60 | 73 | 10 |
| | | | 5 | 60 | 72 | 12 |

It will be noted that all the test compounds give improved GW and SPF values relative to the control. In the case of Examples 18 an 19, excellent SPF values are obtained with no flourescence, which combination of effects is valuable for detergent colour care formulations.

EXAMPLES 20 TO 24

Separate samples of bleached cotton cretonne are padded (80% liquor uptake) with an aqueous bath containing:

10 g/l $Na_2SO_4.H_2O$ and sufficient test compound to provide a concentration of 0.1% or 0.2% by weight of active test compound on the cotton substrate.

As the respective test compounds are insoluble in water, they are added as a 1%, 2.5% or 5% (w/w) aqueous dispersion. This dispersion is obtained by milling 1%, 2.5% or 5% of the respective test product and 1% of Pluronic F 108 (polypropylene glycol containing 80% ethylene oxide) in the presence of glass beads in deionised water.

Drying of the treated cotton samples is effected at 80 C. for 2 minutes, followed by thermofixing for 1 minute at 170 C.

In order to evaluate the wash fastness of the treated cotton samples, the respective samples are washed once, five or ten times in an aqueous bath containing 7 g/l of the standard ECE detergent described in Example 15. Each wash is conducted at 60 C. for 15 minutes at a liquor ratio of 1:10.

The results obtained are set out in the following Table 4:

TABLE 4

| Example | Test compound | Concn. of test compound | number of washes | SPF | GW |
|---|---|---|---|---|---|
| — | none (control) | — | 0 | 5 | 69 |
| | | | 1 | 5 | 67 |
| | | | 5 | 4 | 84 |
| | | | 10 | 4 | 84 |
| 20 | compound of Example 2 | 0.1% | 0 | 28 | 84 |
| | | | 1 | 28 | 180 |
| | | | 5 | 27 | 193 |
| | | | 10 | 29 | 195 |
| 21 | compound of Example 7 | 0.2% | 0 | 30 | 49 |
| | | | 1 | 29 | 26 |
| | | | 5 | 35 | 30 |
| | | | 10 | 38 | 28 |
| 22 | compound of Example 8 | 0.2% | 0 | 30 | -4 |
| | | | 1 | 44 | 11 |

TABLE 4-continued

| Example | Test compound | Concn. of test compound | number of washes | SPF | GW |
|---|---|---|---|---|---|
|  |  |  | 5 | 48 | 16 |
|  |  |  | 10 | 42 | 20 |
| 23 | compound of Example 5 | 0.2% | 0 | 32 | 112 |
|  |  |  | 1 | 37 | 173 |
|  |  |  | 5 | 36 | 206 |
|  |  |  | 10 | 33 | 219 |
| 24 | compound of Example 6 | 0.2% | 0 | 46 | 110 |
|  |  |  | 1 | 40 | 130 |
|  |  |  | 5 | 36 | 133 |
|  |  |  | 10 | 31 | 130 |

It will be noted that all the test compounds give improved SPF values relative to the control. in the case of Examples 21 and 22, excellent SPF values are obtained with no flourescence, which combination of effects is valuable for colour care formulations.

We claim:

1. A method for increasing the SPF rating of textile fibres, comprising treating the textile fibres with 0.05 to 3.0% by weight, based on the weight of the textile fibres, of one or more compounds having the formula (1A):

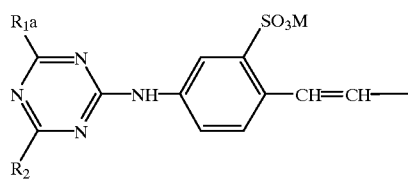

(1A)

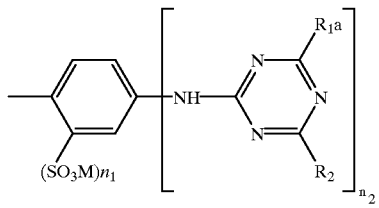

in which $R_2$ is hydrogen, optionally substituted alkyl, optionally substituted aryl,

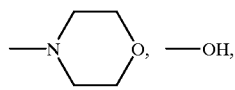

$-NH_2$, $-N(CH_2CH_2OH)_2$, $-N(CH_2CH(OH)CH_3)_2$, $-NH-R_4$, $-N(R_4)_2$ or $-OR_4$, in which $R^4$ is M, optionally substituted alkyl or optionally substituted aryl;

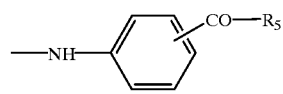

in which $R_5$ is hydrogen, optionally substituted alkyl, optionally substituted aryl or $-NR_7R_8$ in which $R_7$ and $R_8$, independently, are hydrogen, optionally substituted alkyl or optionally substituted aryl, or $R_7$ and $R_8$, together with the nitrogen atom to which they are attached, form a heterocyclic residue;

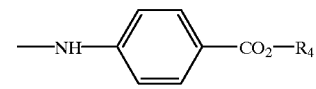

in which $R_6$ is hydrogen, optionally substituted alkyl or optionally substituted aryl, provided that $R_6$ is not carboxymethyl or hydroxymethyl;

$n_1$ and $n_2$, independently, are 0 or 1;

M is hydrogen, an alkali metal atom, ammonium or a cation formed from an amine and $R_1a$ is a group having one of the formulae:

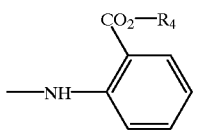

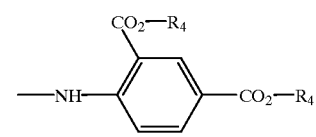

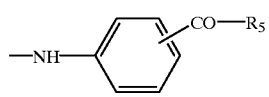

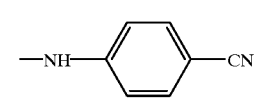

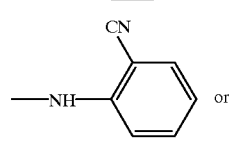

in which $R_4$ and $R_5$ are as previously defined.

2. A method according to claim 1 in which the textile fibres treated are cotton, viscose, flax, rayon, linen, wool, mohair, cashmere, angora, silk, polyester, polyamide or polyacrylonitrile fibres.

3. A method according to claim 2 in which the textile fibres treated are cotton, polyamide or wool fibres.

4. A method according to claim 1 in which the textile fibres treated have a density of less than 200 g/m² and have not been previously dyed in deep shades.

5. A method according to claim 1 in which compound of formula (1A) is only sparingly soluble in water and is applied in dispersed form.

6. A method according to claim 1 in which, in addition to the compound of formula (1A), one or more adjuvants is also employed, said adjuvants being selected from the group consisting of emulsifiers, perfumes, bleaching agents, enzymes, colouring dyes, opacifiers, optical whitening agents, bactericides, nonionic surfactants, fabric softeners, stain release ingredients, stain repellent ingredients, water proofing agents, anti-gelling agents and corrosion inhibitors.

7. A method according to claim 6 in which the amount of each of the adjuvants does not exceed 1% by weight of the treated fiber.

8. A method for increasing the SPF rating of textile fibres according to claim 1 comprising washing the textile fibres with a detergent containing at least one compound of formula (1A), to impart an improved sun protection factor to the washed fibres.

9. A method according to claim 8 comprising washing the textile fibres at least once with the detergent composition at a temperature ranging from 10 to 100° C.

10. A method according to claim 9 comprising washing the fibres material at least once with the detergent composition at a temperature ranging from 15 to 60° C.

11. A textile fabric produced from a fibre treated according to a method as claimed in claim 1.

12. A detergent composition comprising:
   i) 5–90% of an anionic surfactant and/or a nonionic surfactant;
   ii) 5–70% of a builder;
   iii) 0–30% of a peroxide;
   iv) 1–10% of a peroxide activator and/or 0.1–3% of a bleaching catalyst;
   v) 0.005–2% of at least one compound of formula (1A); and
   vi) 0.005–10% of one or more auxiliaries, each by weight, based on the total weight of the detergent;

wherein the compound of formula (1A) is represented by the general formula (1A)

in which $R_2$ is hydrogen, optionally substituted alkyl, optionally substituted aryl, $-NH_2$, $-N(CH_2CH_2OH)_2$, $-N(CH_2CH(OH)CH_3)_2$, $-NH-R_4$, $-N(R_4)_2$ or $-OR_4$, in which $R_4$ is M, optionally substituted alkyl or optionally substituted aryl;

in which $R_5$ is hydrogen, optionally substituted alkyl, optionally substituted aryl or $-NR_7R_8$ in which $R_7$ and $R_8$, independently, are hydrogen, optionally substituted alkyl or optionally substituted aryl, or $R_7$ and $R_8$, together with the nitrogen atom to which they are attached, form a heterocyclic residue;

in which $R_6$ is hydrogen, optionally substituted alkyl or optionally substituted aryl, provided that $R_6$ is not carboxymethyl or hydroxymethyl;

$n_1$ and $n_2$, independently, are 0 or 1;

M is hydrogen, an alkali metal atom, ammonium or a cation formed from an amine and $R_1a$ is a group having one of the formulae:

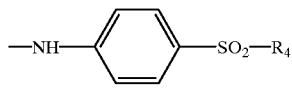

in which $R_4$ and $R_5$ are as previously defined.

13. A detergent composition according to claim 12 comprising:
   i) 5–70% of an anionic surfactant and/or a nonionic surfactant;
   ii) 5–40% of a builder;
   iii) 1–12% of a peroxide;
   iv) 1–6% of a peroxide activator and/or 0.1–3% of a bleaching catalyst;
   v) 0.01–1% of at least one compound of formula (1A); and
   vi) 0.1–5% of one or more auxiliaries, each by weight, based on the total weight of the detergent.

14. A method for the protection of human skin from sunlight which comprises covering the skin with an article of clothing which is a textile fabric which has been treated with 0.05 to 3.0% by weight, based on the weight of the textile fabric of a detergent composition according to claim 12.

15. A method for increasing the tear resistance and/or light fastness of textile fibres, comprising treating the textile fibres with 0.05 to 3.0% by weight, based on the weight of the textile fibres of a detergent composition according to claim 12.

16. A process for the fluorescent whitening of textile materials or paper comprising contacting the textile materials or paper with 0.05 to 3.0% by weight, based on the weight of the textile or paper materials, of at least one compound of formula (1A);

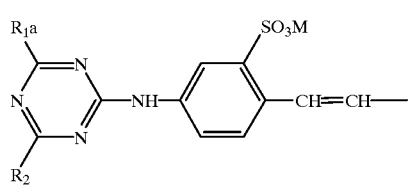

(1A)

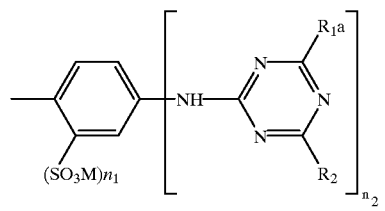

in which $R_2$ is hydrogen, optionally substituted alkyl, optionally substituted aryl,

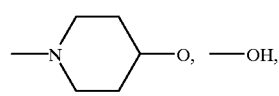

—$NH_2$, —$N(CH_2CH_2OH)_2$, —$N(CH_2CH(OH)CH_3)_2$, —$NH$—$R_4$, —$N(R_4)_2$ or —$OR_4$, in which $R_4$ is M, optionally substituted alkyl or optionally substituted aryl;

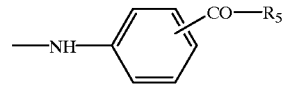

in which $R_5$ is —$NR_7R_8$ in which $R_7$ and $R_8$, independently, are hydrogen, optionally substituted alkyl or optionally substituted aryl, or $R_7$ and $R_8$, together with the nitrogen atom to which they are attached, form a heterocyclic residue;

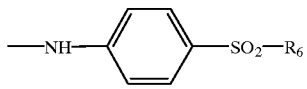

in which $R_6$ is hydrogen, optionally substituted alkyl or optionally substituted aryl, provided that $R_6$ is not carboxymethyl or hydroxymethyl;

$n_1$ and $n_2$, independently, are 0 or 1;

M is hydrogen, an alkali metal atom, ammonium or a cation formed from an amine and $R_1a$ is a group having one of the formulae:

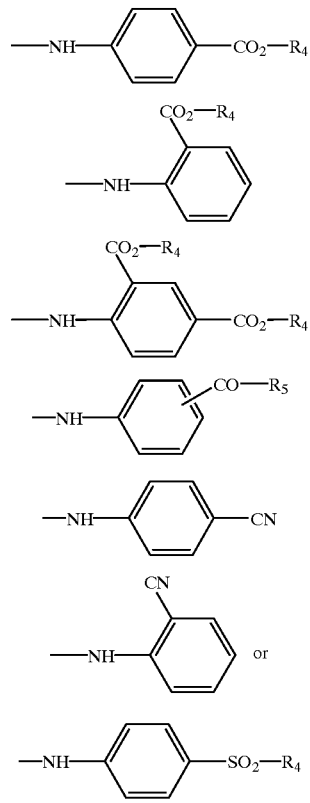

in which $R_4$ and $R_5$ are as previously defined.

17. A textile detergent or softener color care composition comprising 0.005 to 2% by weight, based on the total weight of the composition, of a compound of formula (1A):

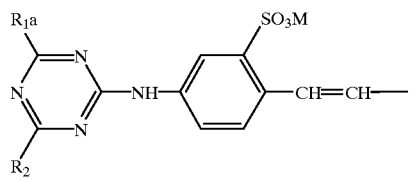
(1A)

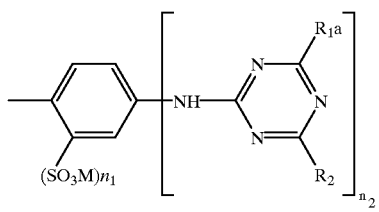

in which $R_2$ is hydrogen, optionally substituted alkyl, optionally substituted aryl,

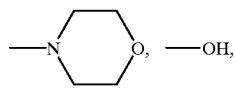, —OH,

—$NH_2$, —$N(CH_2CH_2OH)_2$, —$N(CH_2CH(OH)CH_3)_2$, —NH—$R_4$, —$N(R_4)_2$ or —$OR_4$, in which $R_4$ is M, optionally substituted alkyl or optionally substituted aryl;

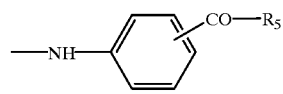

in which $R_5$ is hydrogen, optionally substituted alkyl, optionally substituted aryl or —$NR_7 R_8$ in which $R_7$ and $R_8$, independently, are hydrogen, optionally substituted alkyl or optionally substituted aryl, or $R_7$ and $R_8$, together with the nitrogen atom to which they are attached, form a heterocyclic residue;

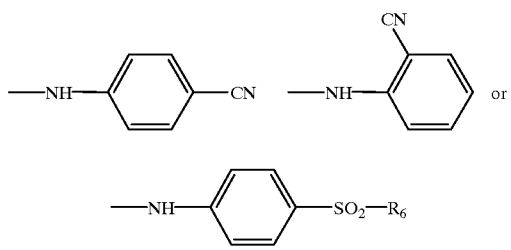 or in which $R_6$ is hydrogen, optionally substituted alkyl or optionally substituted aryl, provided that $R_6$ is not carboxymethyl or hydroxymethyl;

$n_1$ and $n_2$, independently, are 0 or 1;

M is hydrogen, an alkali metal atom, ammonium or a cation formed from an amine and $R_6a$ is a group having one of the formulae:

-continued

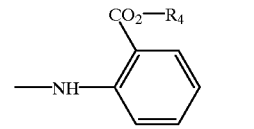

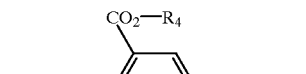

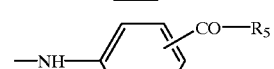

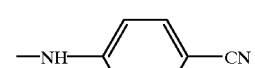

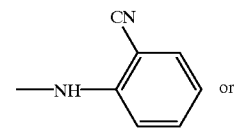 or

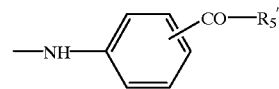

in which $R_4$ and $R_5$ are as previously defined.

18. A composition according to claim 17 in which the compound of formula (1A) is non-fluorescent and contains a group $R_1$ and/or $R_2$ having the formula

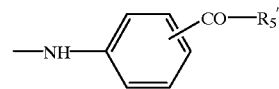

in which $R_5$ is hydrogen, optionally substituted alkyl or optionally substituted aryl.

19. A method for increasing the SPF rating of a textile fiber material comprising washing the textile fiber material with a detergent composition comprising;

i) 5–90% of an anionic surfactant and/or a nonionic surfactant;

ii) 5–70% of a builder;

iii) 0–30% of a peroxide;

iv) 0–10% of a peroxide activator and/or 0–1% of a bleaching catalyst;

v) 0.005–2% of at least one compound of formula (1A); and vi) 0.005–10% of one or more auxiliaries, each by weight, based on the total weight of the detergent, wherein the amount of the detergent composition employed is sufficient to provide 0.05 to 3.0% by weight, based on the weight of the textile fibres, of at least one compound of formula (1A) which is represented by the general formula:

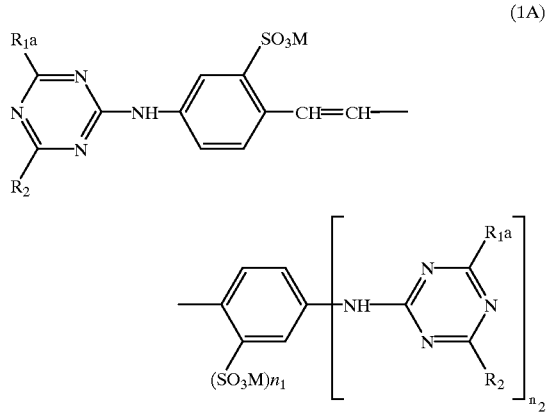 (1A)

in which $R_2$ is hydrogen, optionally substituted alkyl, optionally substituted aryl,

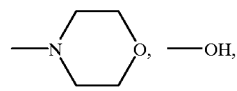, —OH,

—NH$_2$, —N(CH$_2$CH$_2$OH)$_2$, —N[CH$_2$CH(OH)CH$_3$]$_2$, —NH—R$_4$, —N(R$_4$)$_2$ or —OR$_4$, in which $R_4$ is M, optionally substituted alkyl or optionally substituted aryl;

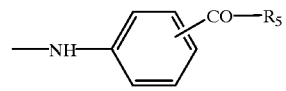

in which $R_5$ is hydrogen, optionally substituted alkyl, optionally substituted aryl or —NR$_7$R$_8$ in which $R_7$ and $R_8$, independently, are hydrogen, optionally substituted alkyl or optionally substituted aryl, or $R_7$ and $R_8$, together with the nitrogen atom to which they are attached, form a heterocyclic residue;

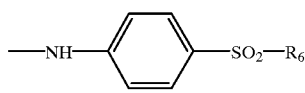

in which $R_6$ is hydrogen, optionally substituted alkyl or optionally substituted aryl, provided that $R_6$ is not carboxymethyl or hydroxymethyl;

$n_1$ and $n_2$, independently, are 0 or 1;

M is hydrogen, an alkali metal atom, ammonium or a cation formed from an amine and $R_1$ is a group having one of the formulae:

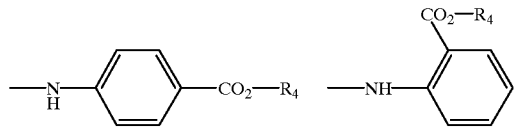

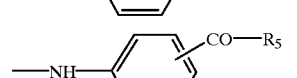

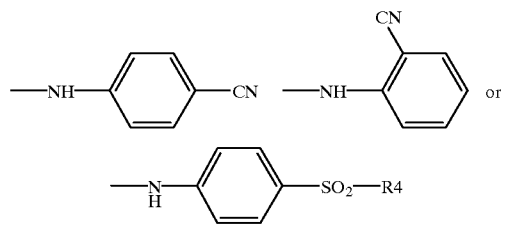 or in which $R_4$ and $R_5$ are as previously defined.

20. A method according to claim 19 in which the detergent composition used comprises:
   i) 5–70% of an anionic surfactant and/or a nonionic surfactant;
   ii) 5–40% of a builder;
   iii) 1–12% of a peroxide;
   iv) 1–6% of a peroxide activator and/or 0.1–3% of a bleaching catalyst;
   v) 0.01–1% of at least one compound of formula (1A); and
   vi) 0.1–5% of one or more auxiliaries, each by weight, based on the total weight of the detergent.

21. A method according to claim 19, in which the detergent is formulated as a solid, as an aqueous liquid containing 5–50% water, or as a non-aqueous liquid detergent containing not more than 5% water.

22. A method according to claim 19 in which the anionic surfactant is a sulphate, sulphonate or carboxylate surfactant, or a mixture thereof.

23. A method according to claim 19 in which the nonionic surfactant is a condensate of ethylene oxide with a $C_9$–$C_{15}$ primary alcohol having 3–8 moles of ethylene oxide per mole.

24. A method according to claim 19 in which the builder is an alkali metal phosphate; a carbonate or bicarbonate; a silicate or disilicate; an aluminosilicate; a polycarboxylate; a polycarboxylic acid; an organic phosphonate; an aminoalkylene poly (alkylene phosphonate); or a mixture thereof.

25. A method according to claim 19 in which the peroxide is an organic or inorganic peroxide compound which bleaches textiles at conventional washing temperatures.

26. A method according to claim 25 in which the peroxide is a persulphate, perborate and/or percarbonate.

27. A method according to claim 19 in which the bleaching catalyst is an enzymatic peroxide precursor and/or a metal complex.

28. A method according to claim 19 in which the detergent contains one or more auxiliaries selected from suspending agents; salts for adjusting the pH; foam regulators; salts for adjusting the spray drying and granulating properties; perfumes; and antistatic and softening agents; enzymes; photobleaching agents; pigments; and shading agents.

* * * * *